United States Patent [19]
Pastan et al.

[11] Patent Number: 5,512,658
[45] Date of Patent: Apr. 30, 1996

[54] PSEUDOMONAS EXOTOXINS (PE) AND CONJUGATES THEREOF HAVING LOWER ANIMAL TOXICITY WITH HIGH CYTOCIDAL ACTIVITY THROUGH SUBSTITUTION OF POSITIVELY CHARGED AMINO ACIDS

[75] Inventors: Ira Pastan, Potomac; David Fitzgerald, Silver Spring; Vijay K. Chaudhary, Rockville, all of Md.

[73] Assignee: The United States of America as represented by the Secretary of the Department of Health and Human Services, Washington, D.C.

[21] Appl. No.: 130,322

[22] Filed: Oct. 1, 1993

Related U.S. Application Data

[63] Continuation of Ser. No. 522,182, May 11, 1990, abandoned.
[51] Int. Cl.$^6$ .......................... C12N 15/31; C07K 14/21; A61K 39/04
[52] U.S. Cl. .................. 530/350; 424/183.1; 424/236.1; 424/260.1; 435/69.7; 435/71.3; 435/875; 435/69.1; 935/11; 530/387.3; 530/391.7
[58] Field of Search .............................. 424/236.1, 183.1; 935/260.1, 11; 435/69.1, 69.7, 71.3, 875; 530/387.3, 391.7, 350

[56] References Cited

U.S. PATENT DOCUMENTS 4,545,985  10/1985  Pastan et al. .............................. 424/85
4,892,827  1/1990  Pastan et al. .............................. 435/193

OTHER PUBLICATIONS

Siegall et al PNAS 85: 9738–9742 (1988) Cytotoxic Activity . . . of IL6–PE fusion protein.
Munro Cell 48: 899–907 (1987) C terminal signal prevents secretion . . . .
Chaudhary Nature (1988) Chaudhary (PNAS) 87:302–312 (1990).
Pastan PNAS (84) 4538–4542 (1987).
Allured, Viloya, S., et al., "Structure of exotoxin A of Pseudomonas aeruginosa at çngstrom resloution", *Proc. Natl. Acad. Sci. USA*, vol. 83, pp. 1320–1324, Mar. 1986.
Chaudhary et al., *Proc. Nat'l Acad. Sci USA Genetics*, vol. 84, Jul., 1987 pp. 4538–4542.
Siegall et al; *J. of Biological Chemistry*, vol. 264, No. 24, Aug., 1989, pp. 14256–14261.
Chaudhary et al., *Proc. Nat'l. Acad Sci USA*, vol. 07, Jan. 1990, pp. 300–312.
Munro et al, *Cell*, vol. 48, Mar., 1987, pp. 899–907.
Chow et al, *J. of Biol. Chem.*, vol. 264, NO. 31, Nov., 1989, pp. 18818–18823.
Waldmann, *J. of Nat'l Cancer Inst.*, vol. 81, No. 12, Jun., 1909, pp. 919–923.
Lorberboum–Galski, *Proc. Nat'l. Acad. Sci USA*, vol. 86, Feb., 1989, pp. 1008–1012.
Lorberboum–Galski, *J. of Biol. Chem.*, vol. 263, No. 35, Dec., 1988, pp. 18650–18656.
Lorberboum–Galski, *Proc. Nat'l Acad. Sci USA*, vol. 85, Mar., 1988, pp. 1922–1926.
Bailon et al., *Biotechnology*, Nov., 1988, pp. 1326–1329.
Ogata et al., *J. of Immunology*, vol. 141, No. 12, Dec., 1988, pp. 4224–4228.
Case et al., *Proc. Nat'l Acad. Sci USA*, vol. 86, Jun., 1909, pp. 281–291.
Siegall et al., *Proc. Nat'l. Acad. Sci. USA*, vol. 85, Dec. 1988, pp. 9738–9742.
Chaudhary et al., *Nature*, 1988.
Hwang et al., *Cell*, Jan., 1987.

*Primary Examiner*—David L. Lacey
*Assistant Examiner*—T. Michael Nisbet
*Attorney, Agent, or Firm*—Townsend and Townsend and Crew

[57] ABSTRACT

Improved Pseudomonas exotoxins of low animal toxicity and high cytocidal activity are described. Substitution of positively charged amino acid residues with an amino acid residue without a positive charge provides markedly changed exotoxins. Conjugation of the new exotoxins with suitable targeting agents provides cytocidal specificity for killing desired cellular entities.

9 Claims, 7 Drawing Sheets

PSEUDOMONAS EXOTOXINS (PE) AND CONJUGATES THEREOF HAVING LOWER ANIMAL TOXICITY WITH HIGH CYTOCIDAL ACTIVITY THROUGH SUBSTITUTION OF POSITIVELY CHARGED AMINO ACIDS

This is a Continuation of application Ser. No. 07/522,182, filed May 11, 1990, now abandoned.

The present invention is generally related to making recombinant chimeric toxins. More particularly, the present invention is related to devising improved forms of recombinant Pseudomonas exotoxins (rPE) of low animal toxicity (when tested in animals) and high cytocidal specificity when attached to suitable targeting agents. Active chimeric toxins of the nature and properties as described herein have not heretofore been known or reported.

BACKGROUND OF THE INVENTION

Recombinant Pseudomonas exotoxins containing deletions in domain Ia of the native toxin and which exhibit low side effects are described in U.S. Pat. No. 4,892,827. However, the role of individual amino acids, either alone or in combination with other amino acid sequences in various domains of the PE molecule were not known. It has been shown, however, that domain Ia is required for the binding of the PE molecule to the target cells.

SUMMARY OF THE INVENTION

It is, therefore, an object of the present invention to identify amino acid residues or sequence(s) responsible for animal toxicity of the PE molecule.

After having determined the role of specific amino acids affecting the animal toxicity of PE, it is a further object of the present invention to construct new forms of recombinant PE molecules (rPE) of low animal toxicity (when tested in animals) but of greater cytocidal efficacy when conjugated with suitable targeting agents, without substantial effect on other cells.

An additional object of the present invention is to provide an efficient method for killing target cells by preparing a variety of improved, active chimeric toxins.

Other objects and advantages will become evident from the following detailed description of the invention.

ABBREVIATIONS

Various abbreviations, symbols, terminologies and the like used herein are now set forth.

PE-40 means a PE molecule of about 40,000 Mr and domain II is the region necessary for translocation of the toxin into the cytosol (Hwang et al. 1987. Cell 48:129–136).

IL6-PE66-4Glu means a chimeric protein comprising an IL6 and a PE molecule of about 66,000 Mr in which 4 positively charged amino acids have been replaced by glutamic acid (Glu), IL6 being the targeting agent. When the targeting agent is a different entity such as TGFα or CD4 and the like, the chimeric protein is accordingly designated TGFα- or CD4-PE66-4Glu and the like. If the replacing amino acid is not glutamic acid, then the replacing amino acid is named accordingly, such as glycine is designated "Gly" and so on.

When a numbering system is used, such as PE-Glu57Gly 246,247,249, it means that the amino acid at position 57 in the sequence of the native PE has been replaced by glutamic acid and the amino acids at positions 246,247 and 249 have been replaced by glycine (Gly).

When a symbol "Δ" or "D" is used, such as 241–250, or D364–380. it means that the sequence of amino acids following the letter "D" or Δ sign, viz., amino acids 241 through 250 or amino acids 364–380 inclusive in these examples, have been deleted.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 is a schematic representation of the structure of the expression vector for PE mutants. The vector contains sequences encoding PE under a T7 promoter with ribosome binding site that is appropriately placed before the initiation codon (Chaudhary et al, 1988, *Proc. Natl. Acad. Sci. U.S.A.* 85:2939–2943; Studier and Moffatt, 1986, *J. Mol. Biol.* 189:113–130: Rosenberg et al, 1987. *Gene* 56:125–235). Protein expression is achieved by IPTG induction of the cultures of *E. coli* BL21(λDE3) carrying this plasmid. Because of an OmpA signal sequence, the proteins are secreted into the periplasm. In the absence of a signal sequence, they accumulate within the cell. There is a three amino acid extension (ala asn leu) remaining after the processing of the signal sequence. Horizontal solid arrows indicate the direction of the transcription. The residues of PE have been circled and 1 is the first amino acid of mature PE (Gray et al. 1984, *Proc. Natl. Acad. Sci. U.S.A.* 81:2645–2649). The original pVC45 is lacking a T7 transcription terminator (T) as well as a phage origin (f+). Vertical arrow is the site of signal sequence cleavage.

FIG. 2 is a schematic diagram of IL6-PE40 derivatives.

FIG. 3 shows sodium dodecyl sulfate-polyacrylamide gel electrophoresis of PE mutant proteins. Samples were boiled in Lammeli buffer and applied on a 10% Sodium dodecyl-polyacrylamide gel (SDS-PAGE). The proteins were stained with Coomassie Blue R-250. Lanes 1 and 2, PE; 3 and 4, $PE^{Glu57}$; 5 and 6, $PE^{Glu246,247,249}$ (PE66-4Glu); 7 and 8, $PE^{Glu57,246,247,249}$. Lanes 1, 3, 5 and 7 are periplasm samples, Lanes 2, 4, 6 and 8 are Mono Q fractions. Standard molecular weight markers are shown in kDa.

FIGS. 4A–4D show Mono Q profiles of PE mutant proteins. Proteins were expressed using plasmids with phage T7 terminator. Each periplasm sample equivalent to 150 ml of the culture was applied on a Mono Q column (HR 5/5) and the column was eluted with a linear gradient of NaCl (0–400 mM in 20 mM Tris, pH 7.6). Fractions of 1 ml were collected. 4A, PE; 4B, $PE^{Glu57}$; 4C, $PE^{Glu246,247,249}$ and 4D, $PE^{Glu57,246,247,249}$. Vertical arrow indicates the location of the peak of interest.

FIG. 5 shows the cytotoxicity of PE mutants on Swiss 3T3 cells. Various dilutions of proteins were added to Swiss 3T3 cells and the protein synthesis measured. The results are expressed as percent of control where no toxin was added. O—O PE, □—□ PE-Glu57, ■—■ $PE^{Glu246,247,249}$, Δ—Δ $PE^{Glu57,246,247,249}$.

FIG. 6 shows the $NaDodSO_4$/PAGE of expressed IL6-PE40-PE 40 (lane 1), IL6-domainII-PE40 (lane 2), IL6-PE40-IL6 (lane 3), IL6-PE40 (lane 4), IL6-PE40D364–380 (lane 5) and $IL6\text{-}PE66^{4Glu}$ (lane 6). The 10.0% protein gel is stained with Coomassie blue. Molecular masses of the standards are indicated in kDa.

FIG. 7 demonstrates the cytotoxic activity of IL6-PE40 derivatives on U266 cells. Chimeric toxins were added at various concentrations to the cells [5×10⁵ cells/ml] and the [³H] leucine incorporation into cellular protein was measured. IL6-PE40 (o), IL6-PE40-PE40 (●), IL6-domainII-PE40 (X), IL6-PE40-IL6 (□), IL6-PE66$^{4Glu}$ (■).

FIG. 8 shows the results of IL6 competition assay using U266 cells [5×10⁵ cells/ml]. IL6-PE66$^{4Glu}$ and IL6 -domainII-PE40 were added to cells in the presence or absence of 1000 ng rIL6. Cells were incubated 24 hours and protein synthesis was determined similar to cytotoxic assays.

FIG. 9 shows the results of binding displacement assay. IL6 chimeric toxins were added at various concentrations (in similar molar ratios) to cells in the presence of 10 ng $^{125}$I-IL6, rIL6 (o), IL6-PE40 (●), IL6-domain II-PE40 (□), IL6-PE66$^{4Glu}$ (■).

DETAILED DESCRIPTION OF THE INVENTION

Figure 1:
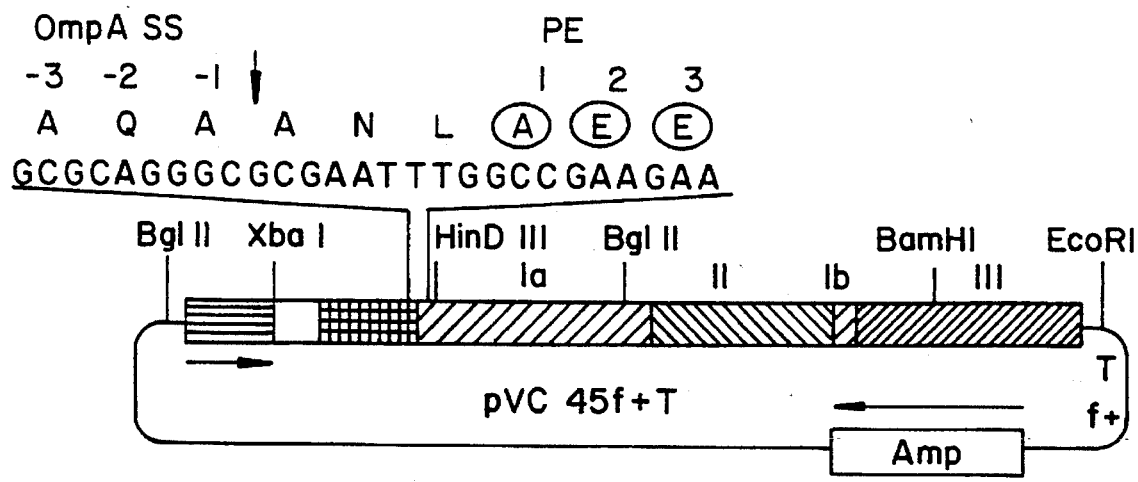
Figure 1:
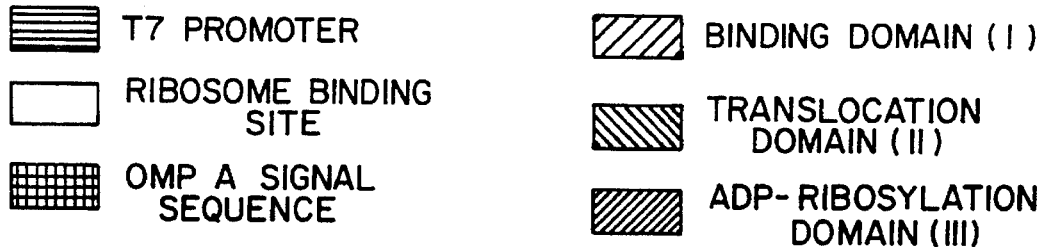

The above and various other objects and advantages of the present invention are achieved by making a plurality of modified recombinant PE molecules containing specific point mutations and various deletions in the amino acid sequences of domain Ia and by preparing a number of chimeric proteins therefrom. Included among such novel molecular entities are PEG$^{lu246,247,249}$, PE$^{Glu57,246,247,249}$, PE$^{Glu57Gly246,247,249}$, PE$^{Glu57}$ Δ241–250, IL6-PE$^{Glu57,246,247,249}$, IL6-domainII-PE40, TGFa-PE66-4Glu, CD4-PE66-4Glu and the like.

It is noted that having exemplified the present invention by the preparation and testing of a plurality of the novel molecular entities mentioned above, various other molecular entities are similarly prepared by the methodologies described herein and are included within the purview of this invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "recombinant" mutant or molecule or PE and the like as used herein means that the mutant, molecule or PE, etc., are not the product of nature, having been deliberately made by the techniques of molecular biology and the like.

The term "without substantial effect" means the normal functions of the cells are not detectably affected.

MATERIALS AND METHODS

Determination of Sequences Responsible for Animal Toxicity: Study of Mutants Mutants were created by standard oligonucleotide-directed mutagenesis (Jinno et al, 1988, *J. Biol. Chem.* 263:13203–13207). DNA fragments containing the mutations were subcloned into PE expression vectors pVC 45 (Chaudhary et al, supra) or pVC 45 f+T (Jinno et al, 1989, *J. Biol. Chem.* 264:15953–15959). Some mutations also introduced new restriction enzyme sites. The mutations were finally confirmed by DNA sequencing using sequenase (United States Biochemicals, address).

Protein Expression and Purification

Cultures of *E. coli* strain BL21(λDE3) carrying the plasmids (Studier and Moffatt, supra) were grown in LB medium containing ampicillin (100 µg/ml). At OD$_{650}$ of 0.6–0.8 the cultures were induced with 1 mM IPTG and shaken for about 90 min at 37° C. The presence of an OmpA signal sequence caused the PE mutant proteins to be secreted into the periplasm. PE was extracted from the periplasm as follows: at the end of the induction period, a 150 ml culture was centrifuged at 2000×g for 10 min and the pellet was suspended in 7.5 ml of sucrose solution (20% sucrose in 30 mM Tris-HCl pH 7.4, 1 mM EDTA) and allowed to stand for 10 min on ice. The sucrose suspension was centrifuged at 5000×g for 10 min and the pellet saved. The pellet was gently suspended in 6 ml of cold water and kept on ice for 10 min, followed by centrifugation at 10,000×g for 10 min. This supernatant (periplasm) was saved and applied on a Mono Q column (HR 5/5) attached to a Pharmacia FPLC. After washing the column with 5 ml of Buffer A (20 mM Tris HCl, pH 7.6), it was developed with a 40 ml linear gradient of NaCl (0–400 mM in Buffer A) followed by a steep gradient of NaCl. The PE mutant proteins were eluted at 0.22–0.26M NaCl.

Analytical Assays and Animal Toxicity

ADP-ribosylation activity was estimated as described by Collier and Kandel (1971, *J. Biol. Chem.* 146:1496–1503). For measuring cytotoxic activities, Swiss 3T3 cells were seeded at 10⁵/ml in 24-well dishes 24 hr prior to the toxin addition. Purified proteins were diluted in Dulbecco phosphate buffered saline (D-PBS) containing 0.2% human serum albumin (HSA) and added to the cells for 16–18 hrs. The cells were pulse-labelled with [³H]-leucine for 90 minutes and the trichloroacetic acid (TCA) precipitable cell-associated radioactivity was determined as a measure of protein synthesis. The results were expressed as percent of control where no toxin was added. SDS/PAGE was performed on 10% gels as described by Laemmli (1970, *Nature* 227:680–685). The protein bands were visualized by staining with Coomassie Blue R-250. The protein concentration was measured by a Coomassie Blue G-250 binding assay (Bio Rad Protein Assay) with bovine serum albumin as a standard.

To test animal toxicity, the purified toxins were diluted in DPBS containing 0.2% HSA and 0.5 ml injected I.P. in 8 week-old mice and 48 hrs later, the number of dead animals was determined.

Expression of PE and Mutant Forms of PE

Figure 4A:
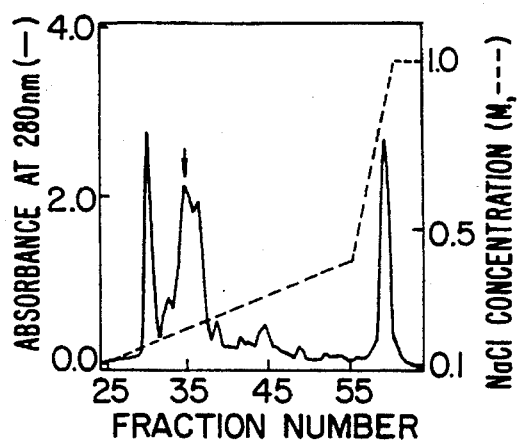
Figure 4B:
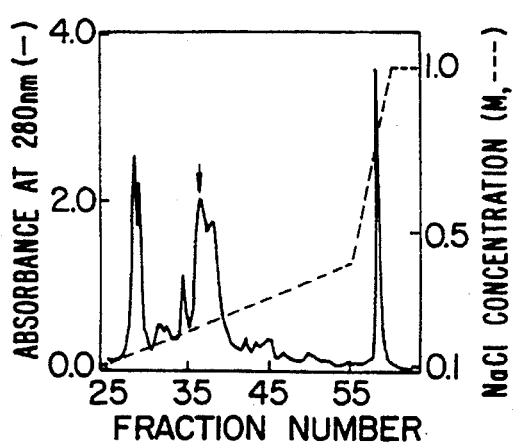
Figure 4C:
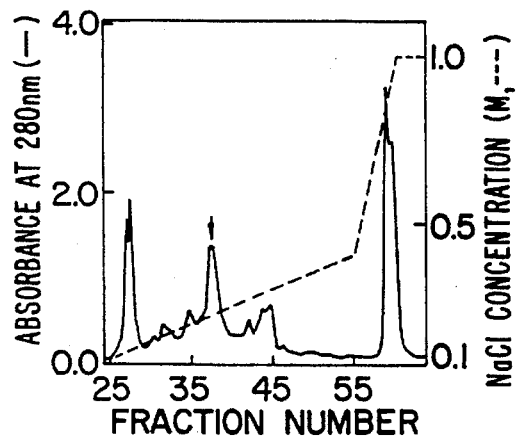
Figure 4D:
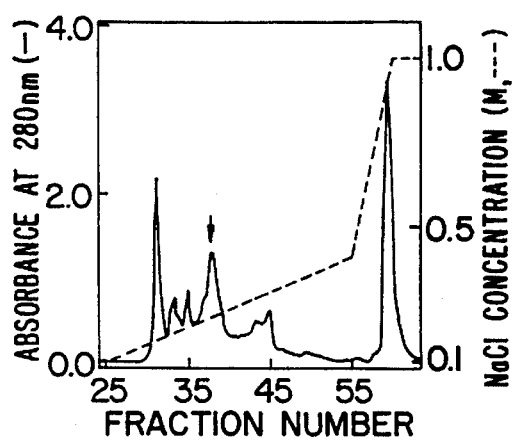
Figure 5:
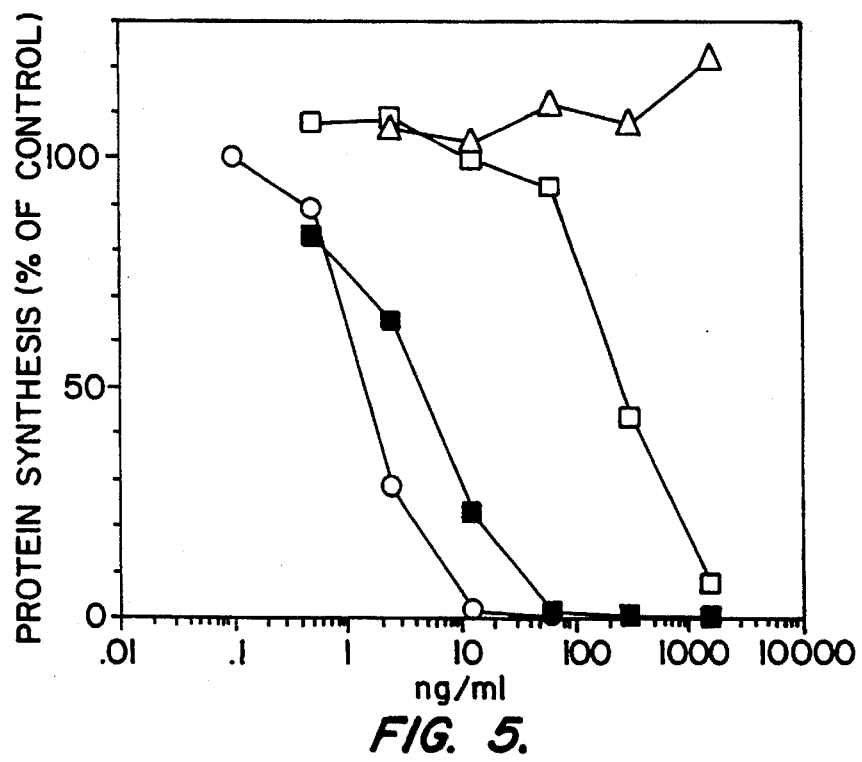

The nucleotide sequences of new mutants are shown in Table I. Proteins with multiple mutations were made by subsequent subcloning. To analyze the cytotoxic activities of the mutant forms of PE in mice and in cell culture, it was necessary to purify large amounts of these molecules to near homogeneity. This was accomplished by constructing a T7 promoter based expression vector in which sequences encoding PE are preceded by an OmpA signal sequence (FIG. 1). Using this vector, large amounts of a soluble form of PE are secreted into the periplasm. In a typical experiment, PE comprises about 20–50% of the protein in the periplasm (FIG. 3), lanes 1,3,5 and 7) and molecules of 70% purity or greater can be obtained by a single ion exchange purification step on Mono Q (FIG. 4A–D and FIG. 3, lanes 2,4,6 and 8). Depending upon the mutation, proteins were eluted at NaCl concentrations of 0.22 to 0.26M. For example $PE^{Glu57,246,247,249}$ which had four basic residues converted to acidic residues, eluted later than PE (FIG. 4A and D). Typical yields from one liter of culture induced at $OD_{650}$ 0.8, range from 15–45 mg of substantially pure (>90% pure) protein (Table II).

Figure 2:
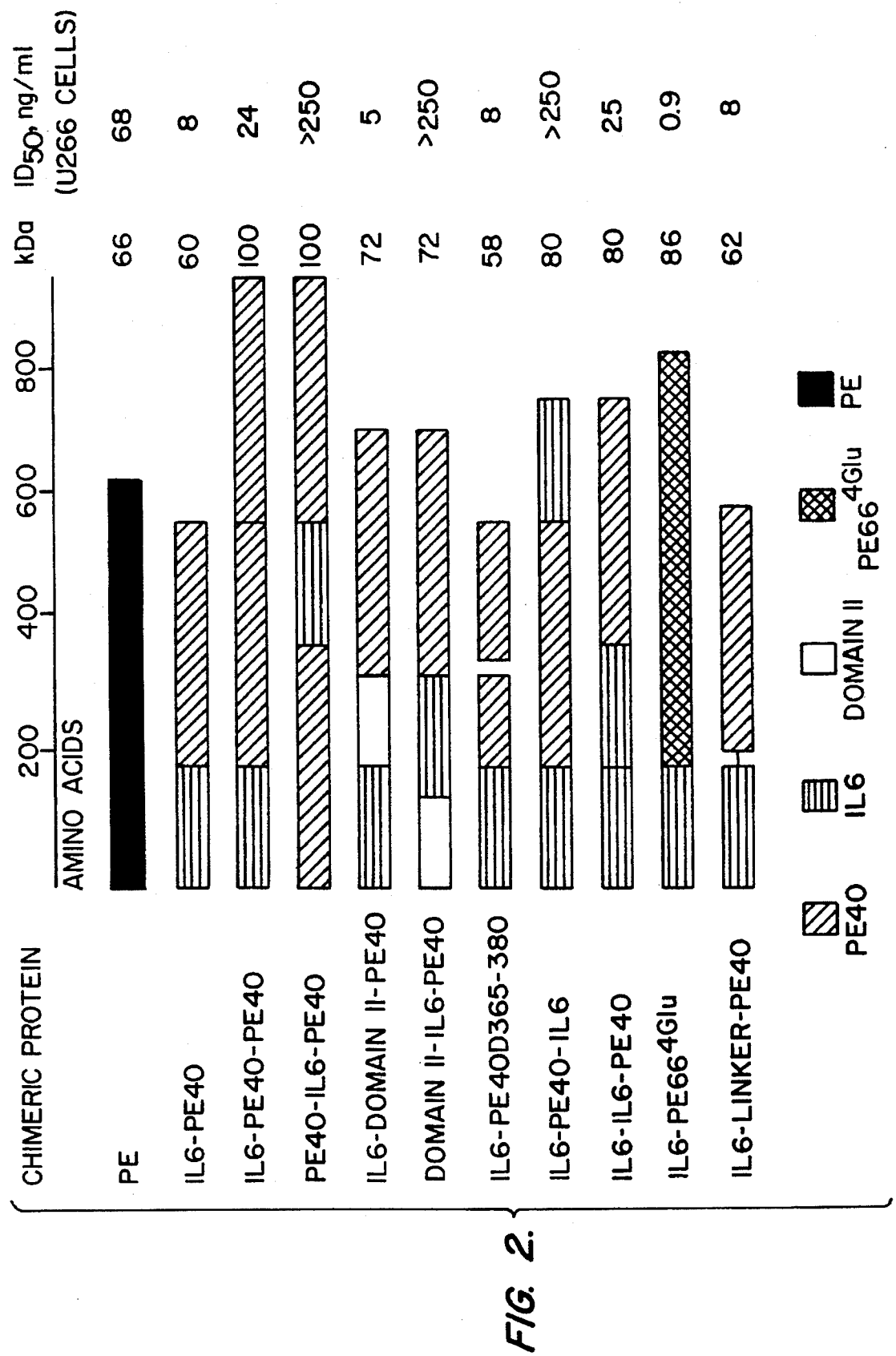
Figure 3:
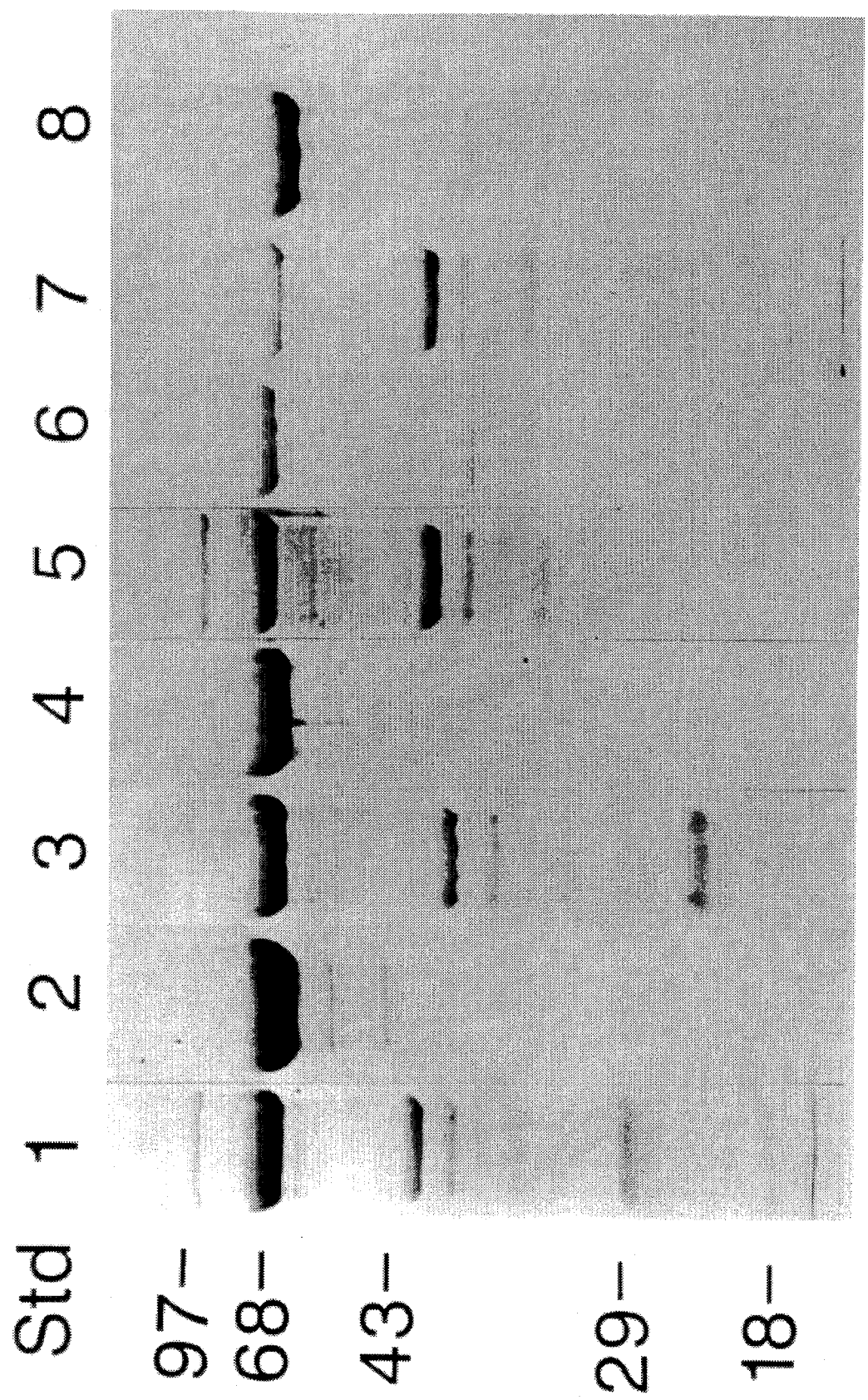

Cytotoxicity and Animal Toxicity of PE and Mutant Forms of PE

As shown in Table III, $PE^{Glu57}$ and PEΔ6-225 had about the same cytotoxic activity on 3T3 cells and the same toxicity for mice ($LD_{50}$=1 μg), whereas PE40 which has a deletion of amino acids 4–252 had no detectable toxicity toward 3T3 cells and had much lower toxicity to mice ($LD_{50}$= 50 μg). To determine more precisely the sequences at the carboxyl end of domain I that were responsible for the high cytotoxic activity of $PE^{Glu57}$ and PEΔ6-225, a series of deletions were created that removed increasing amounts of domain I. The cytotoxic activity of these mutants on 3T3 cells is shown in Table IV. Almost all of domain Ia could be removed without decreasing the activity of these mutants on 3T3 cells. For example, a mutant molecule with deletion of amino acids 6–245 has the same activity as $PE^{Glu57}$. These data indicate that amino acids 246–252 might contribute to the high cytotoxicity. This was confirmed in an experiment in which $Lys^{57}$ was converted to Glu to decrease cell binding and amino acid 241–250 were deleted ($PE^{Glu57\ 241-250}$). This molecule also had no detectable toxic activity towards 3T3 cells (Table IV A–D).

It was noted that carboxyl terminus of domain Ia, that contained three basic amino acids at positions 246, 247 and 249, was hydrogen bonded to amino acids 369, 368 and 367 in domain Ib of Pseudomonas exotoxin (Allured et al, 1986, *Proc. Natl. Acad. Sci. U.S.A.* 83:1320–1324). It was, therefore, decided to explore the role of these basic amino acids in PE mediated toxicity. Accordingly, these amino acids were mutated singly or in combination (Table V and FIG. 5). To do this, a full length PE molecule was utilized in which lysine 57 was converted to glutamic acid to diminish or abolish cell binding through the PE receptor. When the three basic amino acids at 246, 247 and 249 were changed to either glutamic acid or glycine, the cytotoxic activity on 3T3 cells was greatly diminished and reached the level seen with PE40. However, when they were changed individually, no decrease in cytotoxic activity was observed (Table V).

To determine whether the positively charged amino acids at 246 (histidine), 247 (arginine), and 249 (histidine) could be replaced by other charged amino acids, several other substitution mutants were constructed. When all three amino acids were changed to lysines, the cytotoxic activity was unaffected (Table V). In addition, when the two histidines at 246 and 249 were converted to arginines, the cytotoxic effect was also unaffected. However, when glutamic acid was introduced at positions 245, 247 and 248 the cytotoxic effect on 3T3 cells was greatly diminished and the $ID_{50}$ increased to about 600 ng/ml. The cytotoxic activity of the various PE mutants appears to be related to the charge of the amino acids that lie at the carboxyl end on domain Ia (Table V). If only the charge within positions 245 to 249 is considered, it is evident that retaining a net positive charge maintains cytotoxic activity whereas the presence of a neutral or negative charge greatly decreases cytotoxic activity. The toxic activity of various PE mutants was also assessed by injecting several of the purified mutant toxins into mice. As shown in Table VI, only two molecules had low activity in mice. One of these is PE40; the other is $PE^{Glu57,246,247,249}$. Mutation of $Lys^{57}$ to Glu and deletion of a large number of surrounding sequences as in PE 6-229, PE 6-239 and PE 6-245 produced a molecule that had an $LD_{50}$ in mice of about 1 μg. Similarly, in a mutant in which the basic amino acids at 246, 247 and 249 were changed to glutamic acid, and the lysine at position 57 preserved, the $LD_{50}$ in mice was also about 1 μg. Only when the two types of mutations were combined as in $PE^{Glu57,246,247,249}$ was there a large decrease in cytocidal activity and animal toxicity equivalent to deletion of amino acids 4–252 as in PE40.

Cytotoxicity of New Chimeric Proteins: Studies with Il6-PE40 and Derivatives Thereof Enzymes and chemicals were purchased from standard sources. Interleukin 6 was produced and purified as described by Siegall et al, 1990,Mol. Cell Biol. ADP-ribosylation assays were performed as described by Collier et al, 1971, J. Biol. Chem. 246:1496–1503. Radioactive materials were purchased from the Amersham Corporation, Arlington Heights, Ill.

Animals, Cell Lines and Bacterial Strains

For toxicity and serum level assays with IL6-PE40 and derivatives, 8 week old nude mice weighing 18–20 g were used (strain Balb/C; Frederick Cancer Research Facility). H929 and H1112 cells were a gift of A. Gazdar (NCI). All other cell lines were purchased from ATCC (Rockville, Md.). Plasmids were propagated in *E. coli* strain HB101 and expressed in *E. coli* strain BL21 (λDE3) which carries an inducible T7 RNA polymerase gene.

Plasmids

Plasmid pCS68 encoding IL6-PE40 was made as described by (Siegall et al 1989, Proc. Natl. Acad. Sci. USA, 85:9738). To construct IL6-PE40-PE40 and PE40-IL6-PE40, DNA coding for PE40 was removed from the plasmid pVC3875 (Siegall et al 1989, J. Biol. Chem. 264:14256; Siegall et al 1989, FASEB J 3, 2647) and subjected to site directed mutagenesis (Kunkel et al, 1985. Proc. Natl. Acad. Sci. USA. 82:488) which introduced NdeI restriction sites after the last codon in PE40 and prior to the first codon in PE40. The resulting plasmid, pCSA20/A21. was digested with NdeI and the 1080 bp PE40 gene was ligated to the plasmid pCS68 partially cut with NdeI. To construct IL6-domainII-PE40 and domain II-IL6-PE 40, pVC3875 was subjected to site directed mutagenesis which introduced a NdeI restriction site before the first codon of PE40 and after the last codon of domain II coding for amino acid 364. The resulting plasmid, pCSA20/A22 was restricted with NdeI and the 333 bp fragment was ligated to pCS68 which was partially cut with NdeI. To construct IL6-PE 40D364–380, IL6-PE40 was partially digested with SalI, completely digested with BamHI, and ligated to the 500 bp SalI, BamHI fragment from pCS9 (Siegall et al, 1989, J. Biol. Chem. 264: 14256). To construct IL6-PE40-IL6, IL6 was digested with BstXI and BamHI and ligated to an oligonucleotide duplex containing IL6 sequences located proximal to the BstXI site, a segment coding for the amino acids, Ala, Phe, Leu, Asp, Leu, Ala, Val, Val, and the PE sequences located distal and up to the PpuMI site at amino acids 556 in PE. The resulting intermediate vector, pIL6int was cut with PpuMI and EcoRI and the 580 bp fragment was ligated to the 4 kb DNA molecule resulting from similarly digested pCS68. To construct IL6-PE4glu, pCS68 was partially digested with NdeI and completely digested with EcoRI yielding a 3000 bp vector fragment containing the T7 promoter and IL6. The cDNA encoding a full length mutated PE was digested with NdeI and EcoRI and ligated into the similarly digested pCS68 fragment. The mutant PE was carried in the plasmid pJY3All36-1.3 (pVC45/4E). To construct IL6-Linker-PE 40, pCS68 was partially digested with NdeI and completely digested with Bsu36I. An oligonucleotide duplex encoding (Gly$_4$Ser)3 (the linker) and containing the remaining IL6 sequences which follow the Bsu86I site on its 5' end along with sequences to form an NdeI site on its 3' end was ligated into the prepared pCS68 vector. To construct IL6-IL6-PE40, pCS68 was partially digested with NdeI and both the linear (single cut) vector and insert (double cut) band were purified and ligated to each other. FIG. 2 schematically describes the various constructions and Table VII lists a number of plasmids and the corresponding chimeric proteins derived therefrom in accordance with the methodologies described herein.

Expression and Purification of IL6-PE40 and Derivatives

All fusion proteins were expressed in *E. coli* BL21(DE3) followed by isolation and purification from the insoluble fraction (inclusion bodies) of *E. coli* as described by (Siegall et al 1989. Proc. Nat. Acad. Sci. USA. 85:9738). Briefly, after denaturation of the inclusion bodies in 7M guanidine-HCl and renaturation in phosphate buffered saline, the fusion proteins were purified to homogeneity using anion exchange and gel filtration chromatography and the ADP-ribosylation activity of each purified toxin preparation measured by standard methodology.

Cytotoxicity of IL6-PE40 and Related Fusion Proteins

The toxicity of all IL6-toxin fusion proteins was measured by assessing the level of protein synthesis in treated versus non-treated tumor cells used in each experiment (Siegall et al 1989. Proc. Natl. Acad. Sci. USA 85:9738). The chimeric proteins were added in various concentrations to the cells and incubated at 37° C. for 24 hr. Incorporation of [$^3$H] leucine into cellular protein was then measured (Siegall et al 1989, Proc. Natl. Acad. Sci. USA 85:9738). Competition analysis were performed by the addition of rIL6 just prior to the addition of IL6-toxin to the tumor cells.

Receptor Binding Assays

Specific binding of $^{125}$I-IL6 and labeling procedures were performed as described herein above. In these experiments, a fixed tracer amount of $^{125}$I-IL6 (0.5 ng) was added to cells and competed with varying amounts of rIL6 or IL6-toxin. rIL6 and IL6-toxin was adjusted to equal molar amounts using their respective molecular weights. After $^{125}$I-IL6 and competitor were added to the cells, they were incubated for 150 min at 0° C. with gentle agitation every 5 min. The cells were then washed by centrifugation at least three times with a large excess of binding buffer to remove unbound $^{125}$I-IL6. Cell-associated radioactivity was then determined in a Beckman Gamma Counter.

Animal Toxicity and Serum Levels of IL6 Derivatives

Using groups of 2–4 mice, the toxicity of IL6-PE40, IL6-domain II-PE40 and IL6-PE66$^{4Glu}$ was determined. The chimeric toxin was administered intraperitoneally (I.P.) in a single dose and the animals were observed for three days. Serum levels were determined at various times after a single I.P. administration of the chimeric toxins. Bioactivity was measured by determining the cytotoxicity of the serum sample on U266 cells as described herein above. The concentration of the chimeric toxins were estimated by comparisons of the ID$_{50}$ of each serum sample with a standard curve generated by the addition of purified chimeric toxin to U266 cells.

Figure 6:
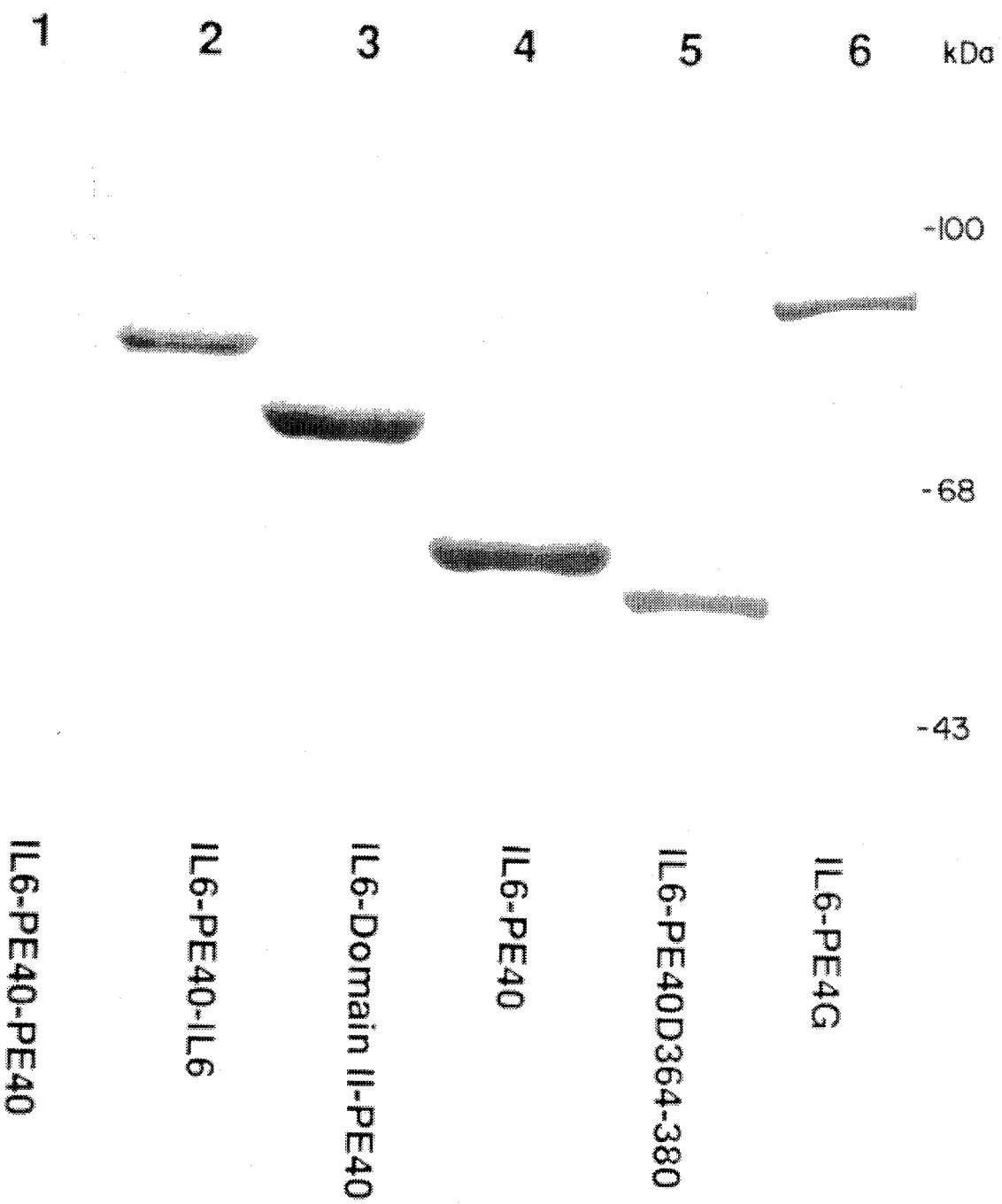

FIG. 6 shows SDS-PAGE patterns of several different chimeric proteins. All the chimeric toxins used in this study were greater than 95% pure and had the expected ADP-ribosylation activity (data not shown).

Cytotoxicity of IL6-PE40 Derivaties

Figures 7, 8:
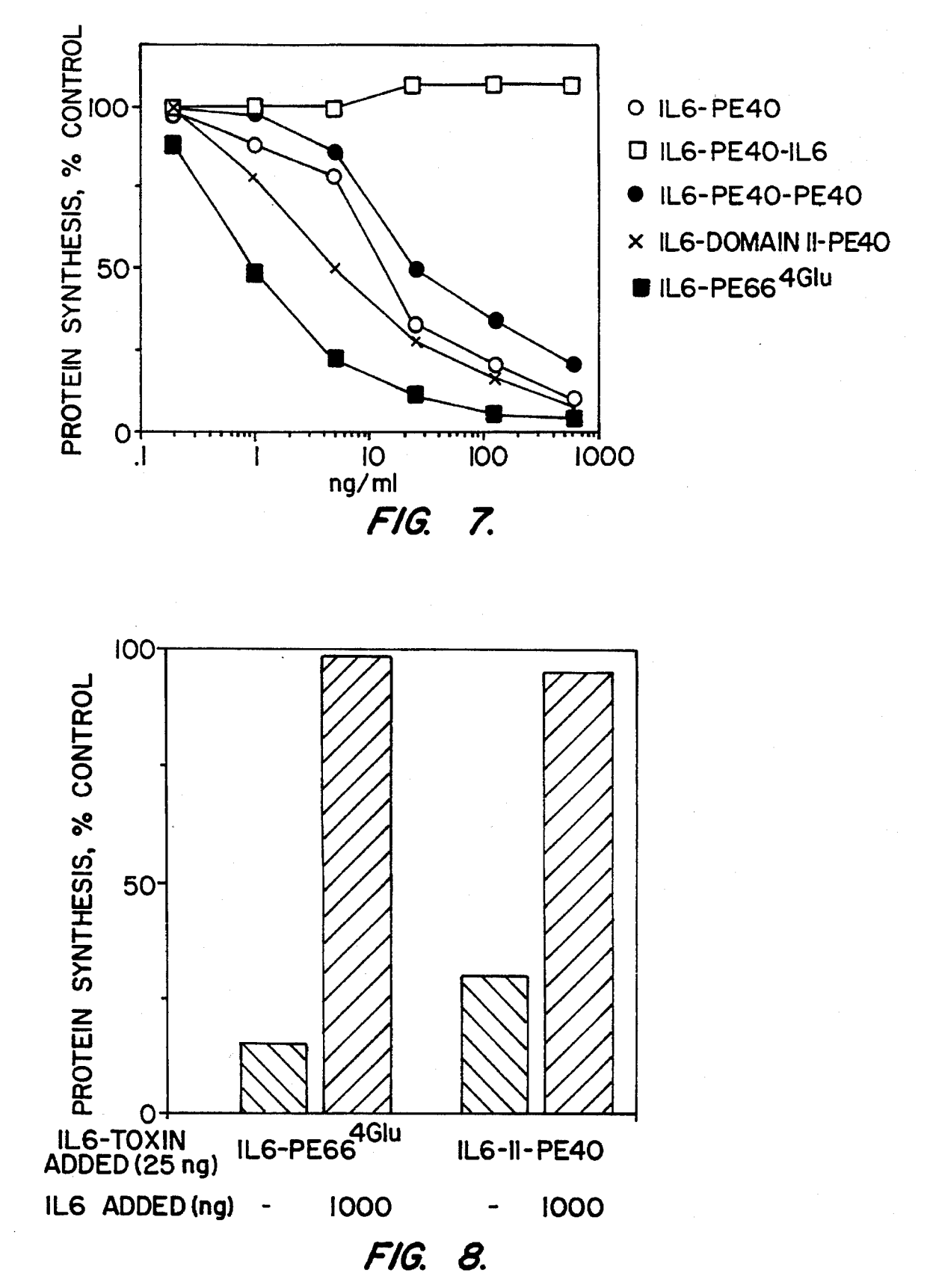

The data shown in FIG. 7 and summarized in Table VII indicate that the IL6-PE40 derivatives fall into four groups based on cytotoxicity to U266 myeloma cells. Group 1 derivaties were more toxic to U266 cells than IL6-PE40, group 2 were of equivalent toxicity to IL6-PE40, group 3 derivaties were about 3-fold less toxic than IL6-PE40 while group 4 derivaties were not toxic to U266 cells.

Group 1 consists of two toxins, the first being IL6-PE 66$^{4Glu}$ which contains IL6 fused to native PE (66 kDa) containing mutations at position 57,246,247 and 249. These amino acids originally coding for Lys, His, Arg and His were each converted to Glu. IL6-PE66$^{4Glu}$ is 8-fold more active than IL6-PE40 on U266 myeloma cells with an ID$_{50}$=1.0 ng/ml (Table VII). The second member of group I is IL6-domain II-PE 40 which is composed of IL6 fused to PE domain II (amino acids 253–364) followed by PE40. Domain II is responsible for processing and translocation of the toxin across cell membranes. IL6-domain II-PE40 is 1.6-fold more active than IL6-PE40 on U266 myeloma cells with an ID$_{50}$=5 ng/ml (Table VII).

Group 2 also contains two members, IL6-PE40D365-380 and IL6-linker-PE40. IL6-PE40D365-380 is composed of IL6 fused to a PE40 molecule with a deletion of amino acids 365–380 (the amino half of domain IB). It was found that the removal of amino acids 365–380 that contain a disulfide bridge increased the activity of TGFα-PE40. In the IL6 version of PE40D365-380 the cytotoxicity to U266 cells was equal to that of IL6-PE40 (ID$_{50}$=8 ng/ml) although this construction produced a larger yield of chimeric toxin than IL6-PE40 (data not shown).

There are two derivatives found in Group 3. IL6-PE40-PE40 is comprised of IL6 fused to two successive PE40 molecules. By doubling the PE40 portion of the fusion protein, it was attempted to increase the cytotoxic activity of the molecule by including two enzymatically active domains. While the new fusion protein IL6-PE40-PE40 was toxic to U266 cells, it was 3-fold less so than IL6-PE40. IL6-IL6-PE40, composed of two adjacent IL6 molecules fused to PE40, was developed in an attempt to increase binding to the IL6 receptor. The cytotoxicity analysis on U266 cells showed that IL6-IL6-PE40 was 3-fold less toxic than IL6-PE40 with an ID$_{50}$ of 25 ng/ml.

Group 4 comprises three members, PE40-IL6-PE40, domain II-IL6-PE40 and IL6-PE40-IL6. The two derivatives PE40-IL6-PE 40 and domain II-IL6-PE40 are similar in that there is either a PE40 molecule or domain II (amino acids 253–364) fused to the amino end of IL6-PE40. Both of these molecules were not toxic to U266 cells ($ID_{50}$>250 ng/ml) and yielded low amounts of protein (data not shown). Since the N-terminus of IL6 was blocked by these additions, the binding of IL6 to its receptor may have been blocked. IL6-PE40-IL6 is comprised of IL6 fused to the amino and carboxyl termini of PE40. This fusion protein was also essentially inactive. This result indicates that IL6 on the carboxyl terminus of PE40 inhibits the toxic activity of the chimeric protein.

Competition of IL6-toxin Derivatives with rIL6 on U266 Cells

To evaluate the binding of the two IL6-PE40 derivatives with increased cytotoxicity on U266 cells to the IL6 receptor, IL6 competition assays were performed. In these experiments, rIL6 was added in excess to compete for the cytotoxic effect of IL6-toxin on U266 cells. As shown in FIG. 8, addition of 1000 ng of rIL6 reduced the cytotoxic activity of 25 ng/ml IL6-PE66$^{4Glu}$ from 15% of protein synthesis to 98% on U266 cells. Similar results were obtained when 25 ng/ml of IL6-domain II-PE40 was used (FIG. 8). These data indicate that both IL6-PE66$^{4Glu}$ and IL6-domain II-PE40 act specifically through the IL6 receptor.

Effect of IL6-PE40, IL6-domain II and IL6-PE66-4$^{Glu}$ on Cells Expressing Different Amounts of IL6 Receptors It has been previously demonstrated that IL6-PE40 was cytotoxic to both myeloma and hepatoma cell lines expressing different numbers of IL6 receptors (Siegall et al 1990 supra). To determine if IL6-domain II-PE40 and IL6-PE66$^{4Glu}$ are more toxic to other cells expressing IL6 receptors, a variety of tumor cells were surveyed. Additionally, the cytotoxicity of PE66$^{4Glu}$ and PE (native) on these same tumor cell lines was determined. These results are summarized in Table VIII.

IL6-domain II-PE40 is more cytotoxic to the hepatoma cell lines PLC/PRF/5, HEP 3B and HEP G2 than IL6-PE40 (Table VIII), IL6-PE66$^{4Glu}$ was more toxic than IL6-domainII-PE40 or IL6-PE40 for the hepatoma cell lines PLC/PRF/5 and HEP G2. Surprisingly, IL6-PE66$^{4Glu}$ is slightly less toxic to HEP 3B cells than either IL6-domainII-PE40 or IL6-PE40. The hepatoma cell line SK-HEP was insensitive to all three IL6-toxin molecules (Table VIII).

The epidermoid carcinoma cell lines A431 and KB were also assessed for their sensitivity to the IL6-toxin chimeras. A431 cells which are insensitive to IL6-PE40 are moderately sensitive to both IL6-domainII-PE40 and IL6-PE 66$^{4Glu}$. The cell line, KB, was insensitive to all IL6-toxin molecules. Additionally, the myeloma cell line H929 was also found to be sensitive to all three IL6 toxins.

The cytotoxicity of native PE and the mutated version of PE, PE66$^{4Glu}$ on these same cell lines was also determined. PE was cytotoxic to all the cell lines tested ($ID_{50}$=5 ng/ml to 68 ng/ml). PE66$^{4Glu}$ was not toxic to any of the cell lines tested ($ID_{50}$>625 ng/ml) indicating its potential usefulness in chimeric molecules (Table VIII). Competition analysis was also performed using rIL6 as competitor on A431 epidermoid carcinoma cells and the hepatoma cell lines PLC/PRF/5 and HEP G2. The results confirm that IL6-domain II-PE40 and IL6-PE66$^{4Glu}$ are IL6 receptor specific (data not shown).

Displacement of $^{125}$I-IL6 by rIL6, IL6-PE40 and Derivatives

Figure 9:
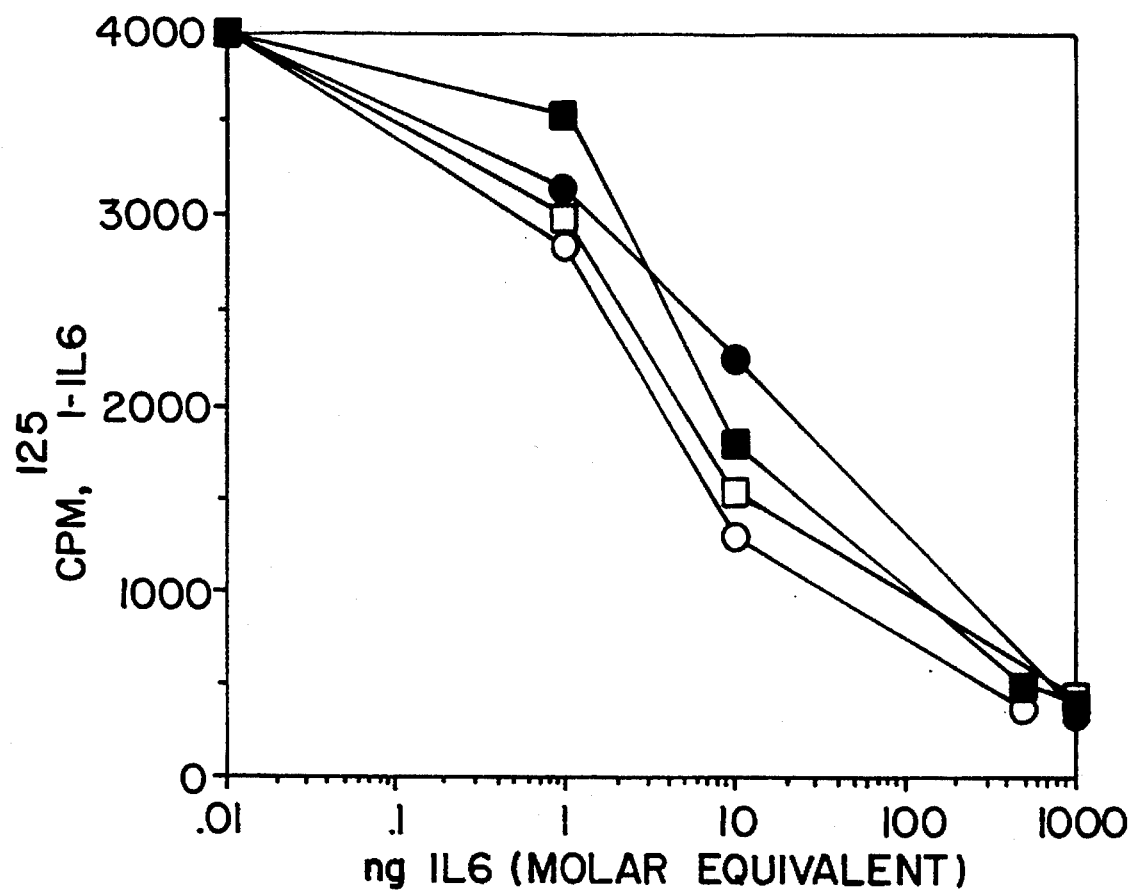

Since the chimeric toxins IL6-domain II-PE40 and IL6-PE 66$^{4Glu}$ were more active than IL6-PE40, it was of interest to determine if the increased activity was due to increased binding. For these experiments, $^{125}$I-IL6 was used as the ligand for the binding analysis. U266 myeloma cells were incubated with 0.5 ng of $^{125}$I-IL6 per 5×10$^6$ cells in 70 μl of binding buffer with or without increasing amounts of added rIL6, IL6-PE40, IL6-domain II-PE40 and IL6-PE66$^{4Glu}$. The results demonstrate that rIL6 displaces $^{125}$I-IL6 from IL6 receptors slightly better than IL6-PE40 (FIG. 9). However, IL6-domain II-PE40 and IL6-PE66$^{4Glu}$ displace $^{125}$I-IL6 approximately the same as IL6-PE40 indicating that the chimeric toxins bind with similar affinities to the IL6 receptor. Therefore, it was concluded that the increased activity of IL6-domain II-PE40 and IL6-PE66$^{4Glu}$ is not due to increased binding to cells, but to another property of the chimeric toxin.

Toxicity of IL6-PE40 and Derivatives in Nude Mice

To determine the potential usefulness of IL6-PE40, IL6-domain II-PE40, and IL6-PE66$^{4Glu}$ as anti-cancer agents, their toxicity in animals was determined. Since nude mice were used to study anti-tumor responses, they were also used to study the toxicity of the chimeric toxins. Mice (2–4 per group) were injected I.P. with single doses of the IL6-toxins in amounts ranging from 5 μg to 50 μg for IL6-PE40, 5 μg to 30 μg for IL6-domain II-PE40 and 5 μg to 20 μg for IL6-PE 66$^{4Glu}$ (Table IX). Animals were observed over 72 hours for mortality. The $LD_{50}$ was 20 μg for IL6-PE40 and IL6-domain II-PE40 and 10 μg for IL6-PE66$^{4Glu}$.

Serum Levels of IL6-toxins in Nude Mice

Nude mice were injected I.P. with IL6-PE40, IL6-domain II-PE40 and IL6PE66$^{4Glu}$ and serum samples were removed at 5 min, 30 min, 1 hr, 2 hr, 4 hr, 8 hr and 24 hr. Serum levels of the chimeric toxins were measured by determining the cytotoxic activity of biologically active material found in the mouse serum at various times after administration. As shown in Table X, IL6-PE40, IL6-domain II-PE40 and IL6-PE 66$^{4Glu}$ all reached peak serum concentrations in 1 hr and were detectable until 8 hr. The peak level was 5 μg/ml, 6 μg/ml and 12 μg/ml for IL6-PE40, IL6-domain II-PE40 and IL6-PE66$^{4Glu}$, respectively.

Tables XI and XII show the properties of the similarly prepared TGFa-PE66–4Glu and CD4-PE66–4Glu.

In summary, the data presented herein clearly show that new, improved Pseudomonas mutants and chimeric toxins with high cytocidal specificity have been obtained. When tested in animals, these recombinantly made chimeric proteins have lower animal toxicity than corresponding unmutated molecules. A target-specific cytocidal composition, in accordance with the present invention, comprises a cytocidal amount of the chimeric toxin of the present invention in a sterile, nontoxic carrier. A method for killing target cells comprises contacting cells desired to be killed, without substantial effect on other cells, with cytocidal amount of the chimeric toxin of the present invention in a single dose or repeated doses. Of course, a targeting agent could be any moiety that recognizes the cells targeted to be killed without substantial effect on other cells. Examples of such targeting agents are antibodies, hormones, cytokines, receptors, growth factors, antigens and the like. It is further noted that although the methodologies described herein are the preferred and the best mode of practising the invention, other methods well known to one of ordinary skill in the art could also be used to obtain the same results and biologically active chimeric toxins etc., as suggested or taught herein.

Deposit

A deposit of plasmids pVC45/4E and pCS64G, from which various chimeric toxins can be made in accordance with the present invention, has been made at the ATCC, Rockville, Md., on Apr. 19 and 23, 1990 under accession numbers 68310 and 68313, respectively. The deposit shall be viably maintained, replacing if it becomes nonviable during the life of the patent, for a period of 30 years from the date of the deposit or for a period of five years from the last date of a request for the deposit, whichever is longer, and upon issuance of the patent, made available to the public without restriction, of course in accordance with the provisions of the law. The Commissioner of Patents & Trademarks shall, upon request, have access to the deposit.

It is understood that the examples and embodiments described herein are for illustrative purposes only and that various changes, routes and modifications In light thereof will be suggested to persons skilled in the art and are to be included within the spirit and purview of this application and scope of the appended claims.

TABLE I

Nucleotide Sequence of mutants

| | | Restriction site created |
|---|---|---|
| A. | | |
| PE | 54 55 56 57 58 59 60 61<br>D A L K L A I D<br>5' GACGCGCTCAAGCTGGCCATCGAC 3' | — |
| $PE^{Glu57}$ | D A L E* L A I D<br>GCGCGCTCGAGCTGGCCATCGAC | XhoI |
| B. | | |
| PE | 243 244 245 246 247 248 249 250<br>V I S H R L H F<br>5' GTCATCAGTCATCGCCTGCACTTT 3' | — |
| $PE^{Glu246}$ | E*<br>GTCATCAGTGAACGCCTGCACTTT | none |
| $PE^{Glu247}$ | E*<br>GTCATCAGTCATGAGCTGCACTTT | none |
| $PE^{Glu249}$ | E*<br>GTCATCAGTCATGAGCTGGAGTTT | none |
| $PE^{Glu246,247,249}$ | E* E* E*<br>GTCATCAGTGAAGAGCTGGAGTTT | none |
| $PE^{Gly246,247,249}$ | G* G* G*<br>GTCATCAGTGGCGGCCTGGGCTTT | none |
| $PE^{Lys246,247,249}$ | K* K* K*<br>GTCATCAGTAAAAAGCTTAAGTTT | HindIII |

Amino acids are shown as single letter code on the top of the nucleotide sequence and mutant amino acids are marked by an asterisk. The numbers indicate the location in PE. The location of new restriction endonuclease clevage sites are indicated by the underlined nucleotides.

TABLE II

Recovery of mutant PE molecules after Mono Q

| Proteins | Amount mg | Purify % |
|---|---|---|
| PE | 46 | >95 |
| $PE^{Glu57}$ | 39 | 95 |
| $PE^{Glu246,247,249}$ | 19 | 70 |
| $PE^{Glu57,246,247,249}$ | 16 | 80 |

*Amount of toxin from one liter of culture induced at OD 650 run of 0.8. The protein concentration was estimated by the Coomassie Blue G-250 protein assay reagent (BioRad) using Bovine serum albumin as a standard.

TABLE III

Toxic Activity of PE and Mutant Forms of PE on Swiss 3T3 Cells and in Mice

| | Toxic Activity | |
|---|---|---|
| Toxin[a] | 3T3 Cells[b] $ID_{50}$ (ng/ml) | Mice[c] $LD_{50}$ (μg) |
| PE | 1 | 0.2 |
| $PE^{Glu57}$ | 100 | 1 |
| PEΔ6-225 | 100 | 1 |
| PEΔ4-252 | >2000 | 50 |

[a]The replacement amino acid with its position is shown as superscript. Δ indicates the deletion of amino acids.

TABLE III-continued Toxic Activity of PE and Mutant Forms of PE on Swiss 3T3 Cells and in Mice

| Toxin[a] | Toxic Activity | |
|---|---|---|
| | 3T3 Cells[b] ID$_{50}$ (ng/ml) | Mice[c] LD$_{50}$ (μg) |

[b]ID$_{50}$ is the concentration of the toxin required to inhibit protein synthesis on Swiss mouse 3T3 cells by 50% as compared to control where no toxin was added. Protein synthesis was measured by [$^3$H]-leucine incorporation in the cells.
[c]LD$_{50}$ is the amount of toxin that kills 50% of the mice within 48 hr after a single I.P. injection.

TABLE IV

Cytotoxic Activity of Domain I Deletion Mutants on 3T3 Cells

| Deletion Mutants | ID$_{50}$ (ng) |
|---|---|
| PE | 1 |
| PE$^{Glu57}$ | 100 |
| PEΔ6-224 | 100 |
| PEΔ6-234 | 120 |
| PEΔ6-239 | 80 |
| PEΔ6-245 | 100 |
| PFΔ4-252 | >2000 |
| PE$^{Glu57}$Δ241-250 | >2000 |

See TABLE III for legends.

TABLE V

Cytotixic Activity of Domain I Point Mutants on 3T3 Cells

| Mutants | ID$_{50}$ (ng) | Charge[a] |
|---|---|---|
| PE | 1 | (+3) |
| PE$^{Glu246,247,249}$ | 3 | (−3) |
| PE$^{Glu57}$ | 100 | (+3) |
| PE$^{Glu57,246}$ | 135 | (+1) |
| PE$^{Glu57,247}$ | 60 | (+1) |
| PE$^{Glu57,249}$ | 60 | (+1) |
| PE$^{Glu57,246,247,249}$ | >2000 | (−3) |
| PE$^{Glu57Gly246,247,249}$ | >2000 | (0) |

TABLE V-continued

Cytotixic Activity of Domain I Point Mutants on 3T3 Cells

| Mutants | ID$_{50}$ (ng) | Charge[a] |
|---|---|---|
| PE$^{Glu57Lys246,247,249}$ | 100 | (+3) |
| PE$^{Glu57Arg246,249}$ | 60 | (+3) |
| PE$^{Glu57\ 245,247,248}$ | 600 | (−1) |
| PE40 | >2000 | |

[a]Charge is based on the number of acidic or basic residues in the region 245 to 250 of PE.

TABLE VI

Toxic Activity of PE Mutants in Mice

| Mutant | LD$_{50}$ (μg) |
|---|---|
| PE | 0.2 |
| PEΔ4-252 | 50 |
| PEΔ6-224 | 1 |
| PEΔ6-239 | 1 |
| PEΔ6-245 | 1 |
| PE$^{Glu57}$ | 1 |
| PE$^{Glu246,247,249}$ | 1 |
| PE$^{Glu57,246,247,249}$ | 30 |

See TABLE III for legends.

TABLE VII

| | Plasmid | Chimeric protein | ID$_{50}$ (ng/ml) | Relative Activity |
|---|---|---|---|---|
| Group 1 | pCS68 | IL6-PE40 | 8–15 | 100 |
| | pCS 64G | IL6-PE66-(4Glu) | 0.9–1.5 | 800 |
| | pCS 6II8 | IL6-domain II-PE40 | 5–10 | 160 |
| Group 2 | pCS 68D14 | IL6-PE40D365-380 | 8–15 | 100 |
| | pCS 6L8 | IL6-Linker-PE40 | 8–13 | 100 |
| Group 3 | pCS 688 | IL6-PE40-PE40 | 24–36 | 33 |
| | pCS 688 | IL6-IL6-PE40 | 25–38 | 32 |
| Group 4 | pCS 868 | PE40-IL6-PE40 | >230 | <2 |
| | pCS II68 | domain II-IL6-PE40 | >250 | <2 |
| | pCS 686 | IL6-PE40-IL6 | >250 | <2 |

ID$_{50}$ is based on protein synthesis using U266 myeloma cells in a 24 hr assay; experiments were done in duplicate or triplicate. Protein is measured by [$^3$H]-leucine incorporation.

TABLE VIII

| CELL LINE (TYPE) | IL6 RECEPTORS PER CELL | ID$_{50}$ (ng/ml) | | | |
|---|---|---|---|---|---|
| | | IL6-PE40 | IL6-II-PE40 | IL6-PE66$^{4Glu}$ | PE66$^{4Glu}$ |
| U266, MYELOMA | 15,500 | 8–15 | 5–10 | 0.9–1.5 | >625 |
| H929, MYELOMA | 16,500 | 8–12 | 5–10 | 1.5–3 | >1250 |
| PLC/PRF/5,HEPATOMA | 2,300 | 5–7 | 3–5 | 1.5–2 | >625 |
| HEP 3B,HEPATOMA | 1,200 | 18–30 | 7.5–20 | 40–50 | >625 |
| HEP G2,HEPATOMA | 200–600 | 450 | 300–400 | 70 | >625 |
| SK-HEP, HEPATOMA | <100 | >623 | >625 | >625 | >625 |
| A431, EPIDERMOID CARC. | ND | >625 | 90 | 80 | >1500 |
| KB, EPIDERMOID CARC. | ND | >625 | >625 | >1250 | >1500 |

ND = NOT DONE
Effects of IL6-toxins on various cell lines expressing different amounts of HA receptors. The ID$_{50}$ listed is a range of 2–4 separate experiments.

TABLE IX

LD$_{50}$ ANALYSIS

| Molecule | Amount Injected | # Deaths/# mice |
|---|---|---|
| IL6-PE40 | 5 μg | 0/4 |
| | 10 μg | 0/4 |
| | 15 μg | 0/2 |
| | 20 μg | 2/4 |
| | 25 μg | 3/4 |
| | 50 μg | 2/2 |
| IL6-II-PE40 | 5 μg | 0/2 |
| | 10 μg | 0/2 |
| | 20 μg | 1/2 |
| | 30 μg | 2/2 |
| IL6-PE66$^{4Glu}$ | 5 μg | 0/2 |
| | 10 μg | 1/2 |
| | 20 μg | 2/2 |

Mice were administered a single dose, I.P. with indicated amounts of IL6-toxin and the number of dead mice were determined after 72 hours.

TABLE X

| Molecule | Size | Amount Injected | Peak | Detection Limit | Maximum Detected |
|---|---|---|---|---|---|
| IL6-PE40 | 60 kD | 15 μg | 1 hr | 8 hr | 5 μg/ml |
| IL6-II-PE40 | 72 kD | 15 μg | 1 hr | 8 hr | 6 μg/ml |
| IL6-PE66$^{4Glu}$ | 86 kD | 15 μg | 1 hr | 8 hr | 12 μg/ml |

Mice were injected I.P. with a single dose and serum levels of the chimeric toxin were determined at 5 min, 30 min, 1 hr, 2 hr, 4 hr, 8 hr and 24 hr by assaying cytotoxic activity on U266 cells. The levels at 8 hr was approximately 0.5 μg/ml

TABLE XI

ACTIVITY OF TGFa-PE-4Glu and CD4(178)PE-4Glu on TARGET CELLS

| | ID$_{50}$ (ng/ml) |
|---|---|
| TGFαPE$^{4Glu}$ | 0.007[a] |
| CD4(178)PE$^{4Glu}$ | 1.5[b] |

[a] on A431 cells in a 20 hr assay.
[b] on CV-1 cells expressing gp120, in a 4 hr assay.

What is claimed is:

1. A recombinant mutant Pseudomonas exotoxin (PE) having a positively charged amino acid residue in domain 1a substituted by an amino acid residue without a positive charge, so that the mutant PE has a lower animal toxicity compared to the unsubstituted molecule, said mutant PE being selected from the group consisting of a PE in which amino acids 57, 246, 247 and 249 are glutamic acid (PE-Glu- 57,246,247,249), a PE in which amino acid 57 is a glutamic acid and amino acids 241–250 are deleted (PE-Glu-57Δ241– 250) and a PE in which amino acid 57 is a glutamic acid and amino acids 246, 247, and 249 are glycine (PE-Glu- 57-Gly246,247,249).

2. A recombinant mutant Pseudomonas exotoxin (PE) attached to a targeting agent which recognizes a specific site on a cell targeted to be killed selected from the group consisting of IL6 attached to a PE in which amino acids 57, 246, 247 and 249 are glutamic acid (IL6-PE 66-4-Glu), an IL6 attached to a PE in which amino acid 57 is glutamic acid and amino acids 246, 247 and 249 are glycine (IL6-PE-Glu-57Gly246,247,249), a TGFα attached to a PE in which amino acids 57, 246, 247 and 249 are glutamic acid (TGFα-PE66-4Glu) and CD4 attached to a PE in which amino acid 57 is glutamic acid and amino acids 246, 247 and 249 are glycine (CD4-PE66-4Glu).

3. The PE of claim 2 being IL6-PE66-4Glu.

4. The PE of claim 2 being IL6-PEGlu57Gly246,247,249.

5. The PE of claim 2 being TGFa-PE66-4Glu.

6. The PE of claim 2 being CD4-PE66-4Glu.

7. A composition comprising a cytocidal amount of the PE of claim 2 and a pharmaceutically acceptable carrier.

8. A recombinant mutant Pseudomonas exotoxin (PE) comprising IL6-domainII-PE40.

9. A composition comprising a cytocidal amount of the recombinant mutant Pseudomonas exotoxin (PE) of claim 8 to kill cells bearing IL6 receptors, and a pharmaceutically acceptable carrier.

* * * * *